United States Patent
Sebastian

[11] Patent Number: 5,372,575
[45] Date of Patent: Dec. 13, 1994

[54] THERAPEUTIC FOREARM APPLIANCE HAVING PRESSURE PAD CONTAINING PARALLEL CHAMBERS

[75] Inventor: Peter R. Sebastian, Salisbury, Md.

[73] Assignee: Safeguard Industrial Corporation, Leesport, Pa.

[21] Appl. No.: 18,320

[22] Filed: Feb. 16, 1993

[51] Int. Cl.$^5$ ............................ A61F 13/00; A61F 5/04
[52] U.S. Cl. ............................. 602/20; 602/13; 602/62; 126/DIG. 20; 606/201
[58] Field of Search .................. 602/13, 20, 62; 128/DIG. 20, 402, 403; 273/29 R, 189 R, 189 A; 473/62; 606/201, 202, 203, 204

[56] References Cited

U.S. PATENT DOCUMENTS

| D. 307,054 | 5/1990 | Johnson, Jr. | D24/190 |
|---|---|---|---|
| 2,028,060 | 1/1936 | Gilbert | 602/13 X |
| 3,789,842 | 2/1974 | Froimson | 602/62 |
| 3,877,426 | 4/1975 | Nirschl | 602/62 |
| 3,942,525 | 3/1976 | Dragan | 602/60 |
| 3,970,081 | 7/1976 | Applegate, Jr. | 128/95.1 |
| 4,027,666 | 6/1977 | Marx | 602/62 |
| 4,048,991 | 9/1977 | Marx | 602/64 |
| 4,168,063 | 9/1979 | Rowland | 473/62 |
| 4,191,373 | 3/1980 | Lancellotti | 273/29 A |
| 4,243,028 | 1/1981 | Puyana | 602/62 |
| 4,441,493 | 4/1984 | Nirschl | 602/62 |
| 4,628,918 | 12/1986 | Johnson, Jr. | 602/13 |
| 4,763,901 | 8/1988 | Richter | 273/29 R |
| 4,807,607 | 2/1989 | Roder | 602/20 |
| 5,063,913 | 11/1991 | Nyl | 602/20 |
| 5,111,810 | 5/1992 | Fortney | 128/402 |
| 5,113,877 | 5/1992 | Johnson, Jr. et al. | 128/882 |
| 5,144,708 | 9/1992 | Pekar | 5/454 |

*Primary Examiner*—Richard J. Apley
*Assistant Examiner*—Beverly A. Meindl
*Attorney, Agent, or Firm*—Wenderoth, Lind & Ponack

[57] ABSTRACT

A therapeutic wrap is securable in an operative orientation around the forearm for relieving stress of the myofascial structures caused by repetitive motion and vibration trauma, such as "tennis elbow". The wrap has a circumference sufficient to encircle the forearm of a user and includes a pocket for accommodating a pressure pad having plural parallel aligned elongate chambers. The parallel aligned chambers of the pressure pad extend lengthwise in a direction parallel to a longitudinal axis of the forearm when the appliance is secured in the operative orientation. The pressure pad may be formed of an air bladder having plural parallel air chambers and a valve mechanism for allowing the user to increase an air pressure contained within the air bladder chambers.

11 Claims, 2 Drawing Sheets

THERAPEUTIC FOREARM APPLIANCE HAVING PRESSURE PAD CONTAINING PARALLEL CHAMBERS

BACKGROUND OF THE INVENTION

1. Field of the Invention

This invention generally relates to a therapeutic appliance for application to the forearm, and more particularly, to a therapeutic wrap having a pressure pad for applying a counterforce pressure to the forearm to relieve stress conditions of the myofascial structure, for example "tennis elbow".

2. Description of the Related Art

The forearm of the human upper extremity is susceptible to injury of myofascial/osseous structures induced by repetitive motion and vibration trauma. The muscular structures as well as their fascial and tendon attachments are frequently the site of pain resulting from muscle tightness, restricted motion and/or inflammation.

A common example of this condition is lateral epicondylitis, commonly known as "tennis elbow". Tennis players, golfers and laborers employing tools, such as repeated hammering and twisting of a screwdriver, are among those frequently affected. Bracing of the affected area is one of the modalities utilized in the treatment of these conditions.

The concept of counterforce bracing has been implemented by devices which encircle the extremity, creating pressure around and against the involved myofascial structures. The theoretical effect of counterforce bracing has been described as disseminating force applied to a muscle over a wider area or reducing force generated by the muscle below a level that would be less likely to induce irritation at its point of attachment to the bone.

Most currently available bracing devices used for this purpose consist of simple elastic or non-elastic bands which encircle the extremity and apply force around the limb in a uniform manner. In addition, a tennis elbow brace is known which utilizes a pre-inflated air pillow held against the involved muscle by an encircling wrap.

However, such conventional bracing devices suffer various drawbacks. The simple elastic or non-elastic band, for example, is deficient since the pressure is uniformly applied and not sufficiently concentrated at the affected area. On the other hand, the above-mentioned pre-inflated air pillow configuration, while perhaps better at concentrating pressure, covers a somewhat limited surface area and can tend to move around along the surface of the forearm during use since it is not particularly adapted to engage the contour of the underlying limb and musculature.

SUMMARY OF THE INVENTION

An object of the present invention is to provide a therapeutic forearm appliance which overcomes the drawbacks of the conventional counterforce bracing forearm wraps.

Another object of the present invention is to provide a therapeutic forearm appliance which concentrates pressure at an affected muscular area of the forearm and which is adapted to follow the contour of the underlying musculature of the forearm.

These and other objects of the present invention are obtained by a therapeutic appliance formed of a forearm wrap having a pocket for accommodating a pressure pad having plural aligned parallel chambers for following the contour of the underlying limb and musculature. Preferably, the pressure pad is a removable inflatable air bladder having parallel air chambers and a valve mechanism by which the air pressure within the chambers can be periodically increased when necessary.

BRIEF DESCRIPTION OF THE DRAWINGS

The features and advantages of the present invention will be more readily understood from the following detailed description of the preferred embodiment with reference to the accompanying drawings in which like parts are designated by like reference numerals and in which.

DETAILED DESCRIPTION OF THE PREFERRED EMBODIMENT

Figure 1:
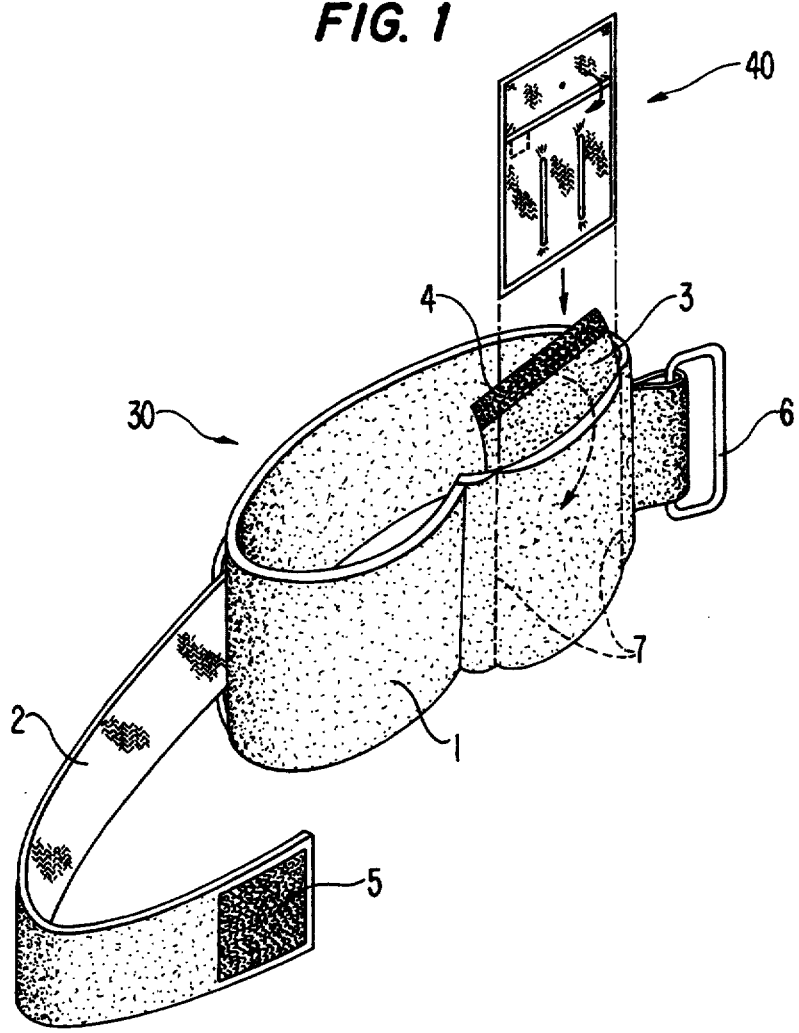
FIGS. 1 and 2 are perspective views of the therapeutic forearm appliance according to the present invention.
Figure 2:
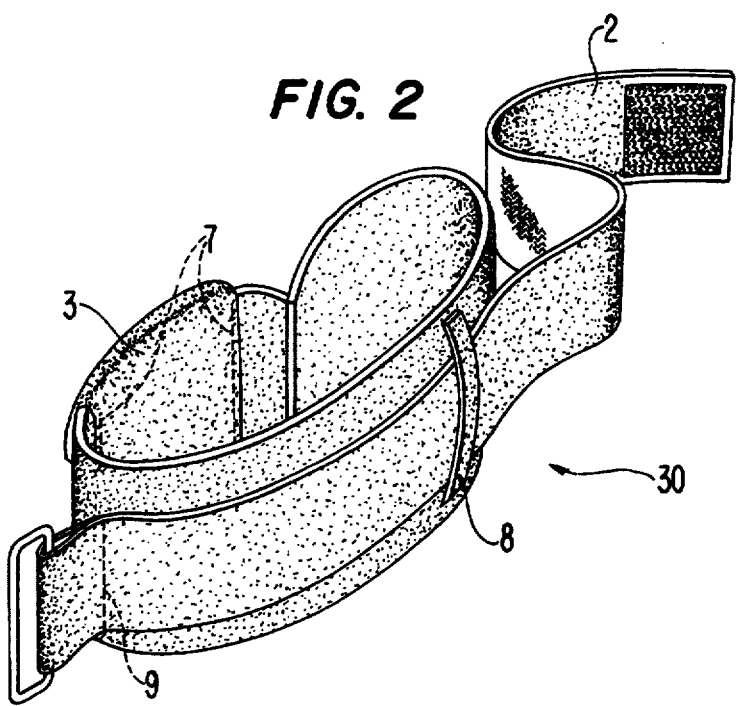
Figure 3:
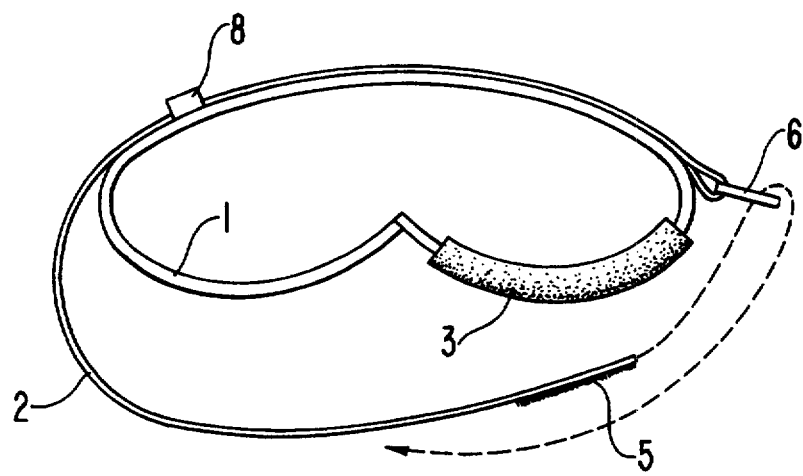
FIG. 3 is a top view of the therapeutic forearm appliance according to the present invention; and, FIG. 4 is a partially cutaway view of a bladder mechanism used as a pressure pad in the therapeutic forearm appliance according to the present invention.

Referring initially to FIG. 1, the therapeutic forearm appliance of the preferred embodiment of the present invention includes two main components, i.e., a pressure pad (inflatable bladder) 40 and a wrap 30. With reference also to FIGS. 2 and 3, the preferred structure of the wrap 30 is first described.

The wrap 30 has a two-layer structure formed of an elastic sleeve 1 (inner layer) and a non-elastic strap 2 (outer layer). The sleeve 1, which lies closest to the user's skin, is fabricated from an elastic neoprene material. The non-elastic strap 2 is secured to the outer surface of the sleeve 1 by stitching 9 and is passed through a loop 8 which is itself secured to the outer surface of the sleeve 1. In the embodiment, the width of the sleeve 1 (extending in a direction perpendicular to circumference of the sleeve 1) is approximately 7.5 cm and the width of the strap 2 is approximately 5 cm.

When the appliance is to be worn, the user slips his or her forearm through the elastic sleeve 1 and positions the sleeve 1 at an appropriate location along the forearm. Even though the elasticity of the sleeve 1 is itself sufficient to hold the appliance in place to some extent, the strap 2 is used to further tighten the appliance around the forearm. In particular, the strap 2 includes a hook-type fastener patch 5 (VELCRO) and a buckle 6 secured at opposite ends thereof. Also, at least a portion of the outer surface of the strap 2 is formed of a loop-type fastener material (VELCRO). As is best shown in FIG. 3 by the dashed arrow, the strap 2 is passed through the buckle 6 and folded back on itself and secured by contact between the hook-type fastener patch 5 and the loop-type fastener material formed on the outer surface of the strap 2. The buckle 6 is positioned over a pocket (described below) of the wrap 30 containing the bladder 40 to avoid irritation to the user's limb from the buckle 6 and to further urge the bladder 40 into engagement with the limb. In this manner, the therapeutic appliance is tightly held against the surface of the user's forearm.

The strap 30 also includes a sheet 3 of material fixed to an inner surface of the sleeve 1 by stitching 7. The sheet 3 and the sleeve 1 define a pocket therebetween having an opening along one edge of the sleeve 1. In the embodiment, the sheet 3 is of sufficient length to extend past the one edge of the sleeve 1 and includes a hook-type fastener 4 fixed along an end thereof. In this manner, the sheet 3 can be folded down to place the hook-type fastener 4 in contact with the outer surface of the sleeve 1 (the outer surface formed a loop-type fastener material) as shown by the dashed arrow in FIG. 1, whereby the opening of the pocket defined by the sheet 3 and sleeve 1 is closed as shown in FIG. 2.

Figure 4:
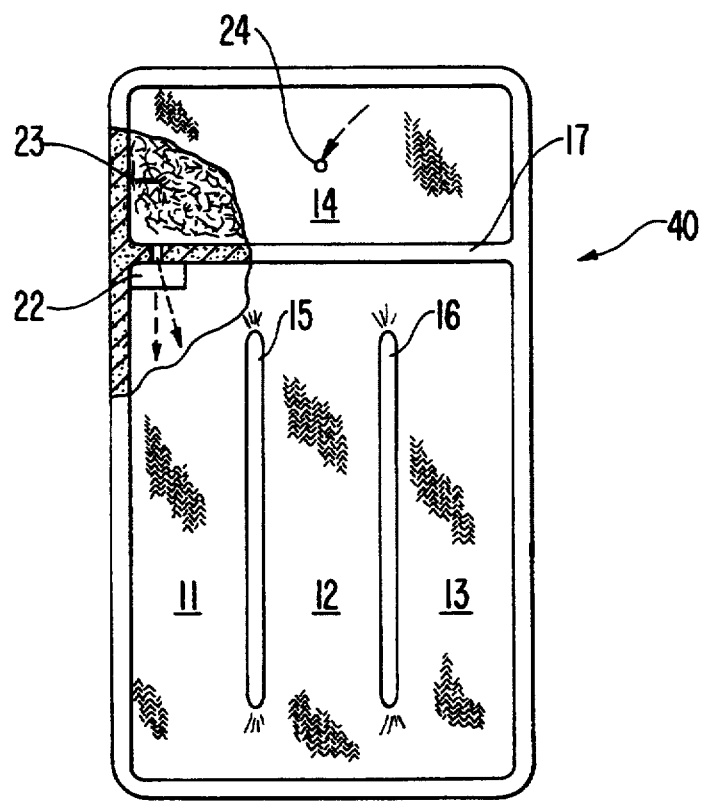

As shown in FIG. 1, the pocket formed by the sheet 3 and the sleeve 1 is for removably accommodating a bladder mechanism 40. (It is noted that the pocket can also be used to accommodate other articles, such as a cold or heat compress.) The details of the bladder mechanism 40 will now be discussed with reference to FIG. 4.

In the embodiment, the bladder mechanism 40 is formed by two generally rectangular sheets of material heat sealed together at their periphery and at seams 15, 16 and 17 to define chambers 11, 12, 13 and 14. In particular, three parallel aligned elongate chambers 11, 12 and 13 are separated by heat sealed seams 15 and 16 throughout most of their length, but remain in continuity with each other through a series of connecting ducts located at opposite ends of the heat sealed seams 15 and 16. The sheet material of the bladder 40 is fabricated from a nylon or plastic vinyl material with low stretchability to allow for repeated reproduction of the same chamber configuration each time the bladder 40 is inflated. In a non-inflated state, the portion of the bladder 40 formed of the three chambers 11, 12 and 13 is approximately 7.5 cm in length (i.e., in a direction parallel to the chamber length), 6 cm in width and 0 cm in thickness. In an inflated state, the same portion of the bladder 40 is approximately 7 cm in length, 5.5 cm in width and 0.75 cm in thickness.

The bladder 40 also includes a fourth chamber 14 aligned perpendicular to the chambers 11, 12 and 13 and located at the proximal end of the bladder 40 which contains a valve mechanism through which the entire bladder is inflated by squeezing it to force air into the bladder chambers 11, 12 and 13 via a one-way air valve 22. The chamber 14 is separated from the remaining chambers by the heat sealed seam 17 and contains a recoverable plastic open-cell foam 23. The recoverable plastic open-cell foam 23 expands the chamber 14 to keep it open whereby air enters the chamber 14 via an entry hole 24. To inflate the chambers 11, 12 and 13, the user places a thumb or finger to cover the entry hole 24 to thereby trap air within the chamber 14 and then squeezes the chamber 14 to cause the trapped air to pass into the chambers 11, 12 and 13 via the one-way air valve 22. In this manner, the chambers 11, 12 and 13 can be maintained at a desired pressure notwithstanding the gradual seepage of air from the chambers over time.

An example of various aspects of the above-described valve mechanism is described in U.S. Pat. No. 5,144,708, which is incorporated herein by reference.

Referring also to FIG. 1, the inflated bladder 40 is placed in the pocket of the wrap 30 such that fourth chamber 14 is folded down at the seam 17 over the outer surface (relative to the surface of the forearm) of the chambers 11, 12 and 13, and such that, when the appliance is worn, the bladder 40 is positioned to urge against the extensor muscle group within the forearm with the parallel chambers 11, 12 and 13 of the bladder 40 aligned parallel to the longitudinal axis of the arm to which it is applied. As such, the parallel aligned chambers follow the contour of the underlying limb and musculature. In this manner, an overall surface pressure area of the limb at the bladder portion of the appliance is increased and any tendency of the appliance to move in a circumferential direction about the limb is reduced.

It is noted that various changes and modifications of the present invention will become apparent to those of ordinary skill in the art upon reviewing the detailed description set forth above. It should be understood, therefore, that such changes and modifications may not depart from the spirit of the present invention defined by the appended claims.

What is claimed is:

1. A therapeutic appliance securable in an operative orientation around the forearm for relieving stress of myofascial structures caused by repetitive motion and vibration trauma, said therapeutic appliance comprising:

a wrap having a pocket formed therein and having a circumference sufficient to encircle the forearm of a user; and, a pressure pad, contained within said pocket of said wrap, having plural parallel aligned chambers extending lengthwise in a direction perpendicular to the circumference of said wrap and parallel to a longitudinal axis of the forearm when the appliance is secured in the operative orientation around the forearm such that the pressure pad follows the contour of the underlying limb and musculature of the forearm to inhibit movement of the appliance around the forearm during use.

2. A therapeutic appliance as recited in claim 1, wherein said pressure pad is an air bladder having plural parallel aligned elongate air chambers.

3. A therapeutic appliance as recited in claim 2, wherein said air bladder contains plural air ducts connecting said plural parallel aligned elongate air chambers such that a body of air contained within said air chambers is contiguous.

4. A therapeutic appliance as recited in claim 3, wherein said pressure pad further comprises an air valve mechanism located at a proximal end of said air bladder, said air valve mechanism operable by the user to increase the air pressure contained within said plural parallel aligned elongate air chambers.

5. A therapeutic appliance as recited in claim 2, wherein said pressure pad further comprises an air valve mechanism located at a proximal end of said air bladder, said air valve mechanism operable by the user to increase an air pressure contained within said plural parallel aligned elongate air chambers.

6. A therapeutic appliance as recited in claim 1, wherein said wrap comprises:

an elastic sleeve containing said pocket along an inner peripheral surface thereof; and an inelastic strap, fixed to and extending along an outer peripheral surface of said elastic sleeve, including a fastener means for tightly securing said elastic sleeve in the operative orientation around said forearm.

7. A therapeutic appliance as recited in claim 2, wherein said wrap comprises:

an elastic sleeve containing said pocket along an inner peripheral surface thereof; and an inelastic strap, fixed to and extending along an outer peripheral surface of said elastic sleeve, including a fastener means for tightly securing said elastic sleeve in the operative orientation around said forearm.

8. A therapeutic appliance as recited in claim 3, wherein said wrap comprises:
an elastic sleeve containing said pocket along an inner peripheral surface thereof; and
an inelastic strap, fixed to and extending along an outer peripheral surface of said elastic sleeve, including a fast fastener means for tightly securing said elastic sleeve in the operative orientation around said forearm.

9. A therapeutic appliance as recited in claim 8, wherein said pocket of said wrap includes an opening for allowing the user to removably insert said pressure pad into said pocket, and wherein said wrap includes a second fastening means for closing said opening of said pocket to secure said pressure pad within said pocket.

10. A therapeutic appliance as recited in claim 1, wherein said pocket of said wrap includes an opening for allowing the user to removably insert said pressure pad into said pocket, and wherein said wrap includes a fastening means for closing said opening of said pocket to secure said pressure pad within said pocket.

11. A therapeutic appliance as recited in claim 6, wherein said wrap includes a sheet of material secured to said elastic sleeve at said inner peripheral surface thereof, said pocket being defined between said sheet of material and said inner peripheral surface of said elastic sleeve, said pocket having an opening at an end of said sheet of material located adjacent a lateral edge of said elastic sleeve, and said sheet of material having a fastener by which said opening of the pocket can be closed by said sheet of material to secure said pressure pad within said pocket.

* * * * *